US012622765B2

(12) United States Patent
Henke et al.

(10) Patent No.: US 12,622,765 B2
(45) Date of Patent: May 12, 2026

(54) STERILIZATION BASKET WITH FIXING HANDLE

(71) Applicant: Aesculap AG, Tuttlingen (DE)

(72) Inventors: Matthias Henke, Villingen-Schwenningen (DE); Sebastian Luz, Emmingen-Liptingen (DE); Ramona Kutscher, Geisingen (DE); Mariana Jakab, Tuttlingen (DE)

(73) Assignee: Aesculap AG, Tuttlingen (DE)

( * ) Notice: Subject to any disclaimer, the term of this patent is extended or adjusted under 35 U.S.C. 154(b) by 335 days.

(21) Appl. No.: 18/037,148

(22) PCT Filed: Nov. 18, 2021

(86) PCT No.: PCT/EP2021/082180
§ 371 (c)(1),
(2) Date: May 16, 2023

(87) PCT Pub. No.: WO2022/112097
PCT Pub. Date: Jun. 2, 2022

(65) Prior Publication Data
US 2024/0000535 A1      Jan. 4, 2024

(30) Foreign Application Priority Data

Nov. 24, 2020      (DE) ..................... 10 2020 131 104.4

(51) Int. Cl.
A61B 50/34      (2016.01)
A61L 2/00      (2006.01)
A61L 2/26      (2006.01)

(52) U.S. Cl.
CPC ............ *A61B 50/34* (2016.02); *A61L 2/0005* (2013.01); *A61L 2/26* (2013.01)

(58) Field of Classification Search
CPC ......... A61B 50/34; A61L 2/0005; A61L 2/26; B65D 25/282; B65D 25/22; B65D 25/32
(Continued)

(56) References Cited

U.S. PATENT DOCUMENTS

| | | | |
|---|---|---|---|
| 4,728,504 A | 3/1988 | Nichols | |
| 9,327,041 B2 * | 5/2016 | Hawkes | ................... A61L 2/26 |

(Continued)

FOREIGN PATENT DOCUMENTS

| | | |
|---|---|---|
| CN | 111824544 A | 10/2020 |
| DE | 10101424 C1 | 6/2002 |

(Continued)

OTHER PUBLICATIONS

Communication received in EP Application No. 21 815 482.1 dated Jun. 9, 2023, with translation, 8 pages.
(Continued)

*Primary Examiner* — Steven A. Reynolds
(74) *Attorney, Agent, or Firm* — Christopher A. Rothe; CM Law

(57) ABSTRACT

A sterilization basket, sterilization basket system and container system. The sterilization basket is insertible into and removable from a container well. At least one basket handle is mounted movably on a basket side wall. The handle has a gripping portion, which is connected to a bearing portion via a connection web oriented at an angle to the gripping portion, on which bearing portion the handle is held on a bearing on the wall of the basket and is movable into at least one carrying position and into a fixing position. The sterilization basket also has at least one fixing and/or pressing portion or element, which is spaced from the gripping portion and mounted on the basket side wall and is movable and/or deformable by a selected movement of the handle
(Continued)

from the basket side wall in the direction outside the sterilization basket to bear against a container well.

14 Claims, 10 Drawing Sheets

(58) Field of Classification Search
USPC .......................... 206/370; 220/756, 769, 770
See application file for complete search history.

(56) References Cited

U.S. PATENT DOCUMENTS

| | | | |
|---|---|---|---|
| 9,393,074 B2 | 7/2016 | Praedel et al. | |
| 2005/0238530 A1* | 10/2005 | Frieze .................... | A61B 50/34 422/1 |
| 2006/0175362 A1* | 8/2006 | Gringer ................. | B65D 25/48 222/570 |
| 2012/0222983 A1* | 9/2012 | Sabounjian .......... | B65D 21/062 206/503 |
| 2014/0216966 A1* | 8/2014 | Ramkhelawan ....... | A61B 50/30 206/370 |
| 2017/0360975 A1* | 12/2017 | White .................... | A61B 50/30 |
| 2018/0028703 A1* | 2/2018 | McLaughlin .......... | A61B 50/34 |
| 2020/0115107 A1* | 4/2020 | Cote .................. | B65D 25/2835 |
| 2021/0259797 A1* | 8/2021 | Görz ......................... | A61L 2/26 |
| 2023/0055196 A1* | 2/2023 | Zieris .................... | A61B 90/90 |

FOREIGN PATENT DOCUMENTS

| | | |
|---|---|---|
| DE | 20317905 U1 | 4/2004 |
| DE | 102012016970 A1 | 3/2014 |
| DE | 102012111096 A1 | 5/2014 |
| KR | 200287392 Y1 | 8/2002 |

OTHER PUBLICATIONS

Search Report received in German Application No. 10 2020 131 104.4 dated Jul. 2, 2021, with translation, 9 pages.
Search Report received in International Application No. PCT/EP2021/082180 dated Feb. 28, 2022, with translation, 5 pages.
Written Opinion received in International Application No. PCT/EP2021/082180 dated Feb. 28, 2022, with translation, 11 pages.
Office Action received in Chinese Application No. 202180078278.9 dated Aug. 13, 2025, with translation, 30 pages.

* cited by examiner

STERILIZATION BASKET WITH FIXING HANDLE

CROSS-REFERENCE TO RELATED APPLICATION(S)

This application is the United States national stage entry of International Application No. PCT/EP2021/082180, filed Nov. 18, 2021, and claims priority to German Application No. 10 2020 131 104.4, filed Nov. 24, 2020. The contents of International Application No. PCT/EP2021/082180 and German Application No. 10 2020 131 104.4 are incorporated by reference herein in their entireties.

FIELD

The present invention relates to a sterilization sieve basket/a sterilization screen basket/a sterilization basket tray/a screen basket tray, in particular a sterilization sieve basket, which is provided and configured for insertion into and removal from a container tray, for which purpose at least one, preferably bow-shaped or arched, sieve basket handle is movably, in particular pivotably, mounted on at least one sieve basket side wall which has a gripping portion for manual gripping, which is connected, via a connection web/bar oriented at an angle to the gripping portion, to a bearing portion, on which the sieve basket handle is held on a bearing on the side of the sieve basket wall and is movable, in particular pivotably, into at least one (first) carrying position/carrying state/gripping state and into a (second) fixed position/fixed state/securing position. The invention also relates to a sterilization sieve basket system and a sterile container system.

BACKGROUND

In healthcare, medical products that come into direct contact with the human body pose a particular risk of infection for the patient. In order to achieve the best possible protection of the patient from infections caused by medical products, high demands are made on the hygienic status of medical products. Critical medical products are required to be sterile, wherein a sterile medical product is free of organisms capable of reproduction, including being free of spores capable of reproduction. For reuse, the products are appropriately processed and sterilized.

Common sterilization processes include heat sterilization processes, either via moist heat or via hot air, low-temperature gas processes, for example ethylene oxide processes, or disinfection processes using aqueous solutions. In these processes, (thermostable) medical products are placed in a sterilization screen basket/sterilization sieve basket/a sterilization basket tray/a screen basket tray for sterilization and are subjected to the corresponding process.

In order to prevent light or small instruments from being thrown out of the sterilization sieve basket or leaving it unintentionally due to other circumstances, in particular during a washing process, and in order to prevent medical products from falling out during transport in sterile barrier systems or on transport trolleys, the sterilization sieve basket is usually provided with an associated, matching sieve basket lid and together forms a sterilization sieve basket system. This closes the sterilization sieve basket and prevents the medical products from leaving the sterilization sieve basket due to its geometry. Normally, a sieve basket lid is placed or respectively put loosely on the sterilization sieve basket for a sterilization sieve basket system with a sterilization sieve basket. Hereafter, two pivotable sieve basket handles of the sterilization sieve basket—which are attached to two opposite inner side surfaces of the sterilization sieve basket, and which were in an upper pivot position/position facing away (gripping position or carrying position) relative to the sterilization sieve basket when the sieve basket lid was placed on it, and which allowed the sieve basket lid to be placed on it—are pivoted downward onto the attached sieve basket lid and finally rest loosely on the sieve basket lid.

According to the prior art, sterilization sieve baskets or sterilization sieve basket systems serve to hold medical or surgical instruments throughout the entire sterile goods cycle, which are packed into a sterile barrier system during a packing process on a clean side of a reprocessing unit for medical products (RUMED/CSSD formerly also called central sterile services department), wherein containers/sterile containers are usually used as the sterile barrier system. Such a sterile container comprises a container tray and a matching container lid, wherein a filter is usually inserted in the container lid in an opening of the container lid in order to provide a defined connection to the external environment with the interposition of the filter with respect to the otherwise hermetically sealed sterile container. In order to be able to place or arrange the sterilization sieve basket or the sterilization sieve basket system in a sterile container, it is generally necessary for the sterilization sieve basket to have smaller geometric outer dimensions than an inner side of the sterile container, since otherwise the sterilization sieve basket would rest on a rim of the sterile container. In other words, the sterile container has to have such geometric internal dimensions (length, width, height) that the sterilization sieve basket or the sterilization sieve basket system with corresponding geometric external dimensions can be completely accommodated in the sterile container. Inevitably, a gap is also required between the inner sides of the sterile container and the outer sides of the sterilization sieve basket to allow good, fast and effective insertion of the sterilization sieve baskets into the sterile container.

However, this circumferential gap between the outer side and the inner side leads to movement of the sterilization sieve basket in the sterile container during transport of the sterile container, for example due to vibrations and accelerations, and to corresponding abrasion of the surfaces rubbing against each other on both the sterilization sieve basket and the sterile container. In addition, such movement may lead to unintended slippage of the contents of the sterilization sieve basket, which in particular may result in damage to the contents. Even (stand) feet attached to the bottom/underside of the sterilization sieve basket cannot completely prevent such slipping and can also wear out over time.

SUMMARY

It is therefore the object of the invention to avoid or at least reduce the disadvantages of the prior art and in particular to provide a sterilization sieve basket, a sterilization sieve basket system, and a sterile container system that provides scratch protection and transport protection, is simple and safe and easy to handle, is in particular well suited for transport and storing, and is durable and wear-resistant. In particular, it offers a user the function of inserting the sterilization sieve basket well manually into a sterile container and fixing it relative to the sterile container and preventing it from slipping, as well as removing the sterilization sieve basket again just as easily, safely and well. In addition, a sieve basket lid is intended to be easily and safely attachable onto the sterilization sieve basket, even when being inserted in the sterile container.

Thus, the core of the present invention is to provide such a sterilization sieve basket which, causally due to the selected movement of the sieve basket handle, i.e. in particular due to the manual manipulation of the gripping portion, consequently moves and/or deforms a specially provided and operatively connected and/or operatively coupled fixing portion and/or press-on portion or element, which in particular is adapted to come into contact as a contact point or contact surface, in the direction outside of the sterilization sieve basket. Thus, by the selected movement of the sieve basket handle, in particular by the movement of the sieve basket handle from the carrying position to the fixed position, the fixing portion and/or the press-on portion or element, which is spaced apart from and thus different from the gripping portion, is moved and/or deformed in the direction outside of the sterilization sieve basket.

The distance between the gripping portion and the fixing portion and/or press-on portion or the element is provided because it prevents interference with manual handling. Due to the distance, a specific function is assigned to the respective portion. The gripping portion is assigned the function of manual gripping and the fixing portion and/or press-on portion or the element is assigned the different function of fixing or pressing.

Thus, by the fact that the sieve basket handle has the gripping portion for manual gripping and handling, which is connected to the bearing portion via a connection web oriented at an angle to the gripping portion and is mounted, in particular hinged, on the sieve basket side wall, in conjunction with the at least one fixing portion and/or press-on portion or element, such a configuration is provided, via which the sterilization sieve basket can abut, press against, connect and/or reduce a distance to an external, i.e. outside of the sterilization sieve basket, (counter) contact surface, contact point and/or contact system by movement and/or deformation.

In particular, the sterilization sieve basket in the carrying position/carrying state of the sieve basket handle has a smaller width and/or depth of two portions facing away from each other as an external dimension than in the fixed position/fixed state of the sieve basket handle. The distance between two defined contact points or (contact) surfaces of the sterilization sieve basket facing away from each other can therefore be changed as a result of the selected movement and thus implicitly as a result of the position/state of the sieve basket handle. At increased distance, these contact points or contact surfaces can, when the sterilization sieve basket is inserted into a container or container tray, for example, rest against an inner wall (or at least reduce the circumferential gap) and fix and secure the sterilization sieve basket. At least one movable and/or deformable contact point or contact surface forms the fixing portion and/or press-on portion or the element. If, for example, two or more contact points or contact surfaces are movable and/or deformable by the selected movement and thus position-dependent of the sieve basket handle in the direction outside of the sterilization sieve basket, then these can also each form the fixing portion and/or press-on portion or the element.

In particular, such a sterilization sieve basket is provided which has a fixing portion and/or press-on portion or element operatively connected or coupled to the sieve basket handle and movable, in particular pivotable, and in particular adapted to come into contact with a surface, a counterpress-on portion or element or a planar plane. Preferably, in the carrying position/carrying state, the fixing portion and/or press-on portion or element may be arranged in the inner volume of the sieve basket, i.e. inside the sterilization sieve basket, and does not to protrude with respect to an outer side of the sieve basket circumferential wall, and can be moved and/or deformed by the selected movement in the direction outside of the sterilization sieve basket, in particular to protrude outward in the fixed position/fixed state with respect to the outer side of the corresponding sieve basket side wall or at least a portion of the outer side. In addition, the fixing portion and/or press-on portion or element may already protrude relative to the outer side and may be moved and/or deformed even further in the direction outside of the sterilization sieve basket by the selected movement. Thus, a dimension of the sterilization sieve basket, in particular the largest dimension, can be changed in one direction, in this case can be increased in height. Preferably, a dimension, in particular the largest dimension, or a distance between two outer surfaces of the sterilization sieve basket or partial sections thereof facing away from each other is increased, so that (two-sided) pressing (actio and reactio) is effected in particular in a container tray.

In yet other words, the sterilization sieve basket comprises at least one fixing portion and/or press-on portion or element spaced from the gripping portion and supported on the at least one sieve basket side wall and movable and/or deformable by selected movement of the sieve basket handle away from the sieve basket side wall in the direction toward the outside of the sterilization sieve basket in order to abut against a container tray.

This configuration of the sterilization sieve basket can provide a user with simple and effective transport protection and scratch protection.

The direction outside of the sterilization sieve basket is a direction (any possible direction) pointing/directed away from an inner volume of the sieve basket toward the outer environment of the sterilization sieve basket. In other words, the direction outside of the sterilization sieve basket points away from the sterilization sieve basket itself. In particular, the direction outside of the sterilization sieve basket has a directional portion in the width and/or depth to cause a change of an abutment point of the fixing portion and/or press-on portions or element in the horizontal plane by the movement. In particular, the direction outside of the sterilization sieve basket may be the width and/or depth direction.

The selected movement is a specific movement of the sieve basket handle. This selected movement may be, for example, a pivoting movement, a rotating movement, a translatory movement as well as a combination of these movements. It is important here that the fixing portion and/or press-on portion or element is causally movable and/or deformable in the direction outside of the sterilization sieve basket due to this selected movement by corresponding operative connection.

The term carrying position/carrying state describes a (first) position/state of the sieve basket handle in which manual grasping and carrying of the sterilization sieve basket 1 is easily possible for a user. In particular, the sieve basket handle extends vertically upward relative to the sterilization sieve basket so that the sieve basket handle can be easily grasped by a user, preferably from above, and can be held in a suspended manner.

The term fixed position/fixed state/spreading position, on the other hand, describes a second position/state of the sieve basket handle, different from the first position, in which the fixing portion and/or press-on portion or the element has been moved and/or deformed further in the direction outside of the sieve basket, in particular a dimension between two defined contact points or contact surfaces has increased in one direction compared to the carrying position and fixes the sterilization sieve basket, in particular when it is inserted in a container tray of a container system, for example against slipping. Preferably, the fixed position is such a position of the movable sieve basket handle in which the sieve basket handle extends substantially horizontally and further preferably inward to the sterilization sieve basket.

The terms width, depth and height are used below as directional indications or axes of a Cartesian coordinate system, wherein width and depth are used as usual for a base surface, such as the sieve basket bottom. The terms 'top' and 'bottom' are used in the direction of height, the terms 'left' and 'right' in the direction of width, and the terms 'front' and 'back' in the direction of depth.

Preferably, a recess, in particular an opening, may be formed in the at least one sieve basket (side) wall in the area of the at least one sieve basket handle, through which the fixing portion and/or press-on portion or the element can be moved and/or deformed by the selected movement of the sieve basket handle in the direction outside of the sterilization sieve basket and, in particular, can project outward in the fixed position relative to the outer side. The recess creates a kind of geometric channel/connection between the outer side and the inner volume of the sieve basket, through which the fixing portion and/or press-on portion or the element (depending on the movement and position of the sieve basket handle) can move in particular. Preferably, the recess is in the form of a rectangular opening with a peripheral border (of the sieve basket wall), which is located in particular at the upper rim portion of the sieve basket wall. Further preferably, the sterilization sieve basket has a recess on each of two opposite sieve basket walls for a respective fixing portion and/or press-on portion or element. In particular, the at least one sieve basket wall has a plurality of recesses for a plurality of fixing portion and/or press-on portions or elements.

According to a preferred embodiment, the sieve basket handle may be pivotably hinged in the manner of a two-sided lever about a pivot joint with a rotational axis, and the sieve basket handle may comprise the fixing portion and/or press-on portion or the element spaced from the rotational axis and the, in particular rod-shaped, gripping portion spaced from the rotational axis for manual gripping of the sieve basket handle, wherein the fixing portion and/or press-on portion or element is arranged on one side of the rotational axis (first side of the lever) and the gripping portion is arranged on the other side of the rotational axis (second side of the lever), so that a pivoting movement of the gripping portion causes a pivoting movement of the fixing portion and/or press-on portion or element about the rotational axis in the same direction. In other words, the sieve basket handle is hinged to the sieve basket wall so as to be rotatable/pivotable about a rotational axis, wherein the gripping portion is arranged on a first side of the two-sided lever and the fixing portion and/or press-on portion or the element is arranged on a second side (opposite to the first side with respect to the rotational axis) of the two-sided lever. Both the gripping portion and the fixing portion and/or press-on portion or the element are arranged at a distance from the rotational axis. The gripping portion is provided and configured to be manually grasped by a hand and to carry the sterilization sieve basket. If the sieve basket handle is now handled and pivoted at its gripping portion, this automatically causes a pivoting movement of the fixing portion and/or press-on portion or element due to the geometry of the sieve basket handle as a two-sided lever. Preferably, the gripping portion is bow-shaped or arched. Preferably, the rotational axis is parallel to (the outer side of) the associated sieve basket wall and/or parallel to a sieve basket bottom. Alternatively, a mechanism, such as a gear transmission, may be provided between the sieve basket handle and the fixing portion and/or press-on portion or element, such as in the form of a rack and pinion gear.

According to a further preferred embodiment, the sieve basket handle may be configured in the form of a straight lever, with arrangement of gripping portion, rotational axis and fixing portion and/or press-on portion or element seen in the direction of the rotational axis in straight extension to each other (similar to a rocker). Additionally or alternatively, a perpendicular distance between the gripping portion (as the line of action of the force) and the rotational axis may be greater by a multiple, in particular 2-fold to 6-fold, in particular 3-fold to 4-fold greater than a perpendicular distance between the fixing portion and/or press-on portion or element and the rotational axis to form an effective lever arm. Alternatively, the two-sided lever may also be configured in the form of a bent lever, for example L-shaped, which uses the fixing portion and/or press-on portion or element in a manner similar to an eccentric tappet.

It may be practical if the sieve basket handle comprises a plurality of fixing portions and/or press-on portions or elements, preferably two or three, which in particular have an equal perpendicular distance between the fixing portion and/or press-on portion or element on the one hand and the rotational axis on the other hand and which are preferably arranged axisymmetrically, i.e. to a symmetry plane perpendicular to the rotational axis. Distributed over, for example, a depth of the sterilization sieve basket, the fixing portions and/or press-on portions or elements can then distribute a force transmission, thereby avoiding local stress peaks and transmitting the force even more homogeneously over a larger section due to an enlarged and distributed area and fixing the sterilization sieve basket even better and more securely.

Preferably, the fixing portion and/or press-on portion or the element may comprise an attachment with inherent elasticity, which preferably comprises rubber, silicone, in particular foam silicone, and/or plastic as material and in particular consists of rubber, silicone, in particular foam silicone, or plastic, wherein the attachment is preferably detachably/interchangeably coupleable to the fixing portion and/or press-on portion or element, in particular is attachable and/or clippable. In this way, the fixing portion and/or press-on portion or the element in the area of the outer contact point may have a different material and design than the rest of the sieve basket handle, which, among other things, improves a production process. The attachment with its inherent elasticity enables tolerance compensation and tensioning with secure positioning of the sterilizing tray handles in particular of the fixed position. If the attachment is detachable, it can be quickly and easily replaced as a wear product. For example, the attachment may be placed on the fixing portion and/or press-on portion or element and then removed as required, for example after a predetermined time interval or number of sterilization processes. Preferably, the attachment may have a coefficient of friction with respect to steel, in particular stainless steel, greater than 0.2, preferably greater than 0.5 more preferably greater than 0.7. Preferably, the attachment may be molded onto the fixing portion and/or press-on portion or the element.

Preferably, the fixing portion and/or press-on portion or the element has a rod-shaped attachment portion with a D-shaped contour or cross-section (circular cross-section with cut-off side) and the attachment has a complementary D-shaped through opening. Thus, when plugged on, the attachment is held on the plug-on portion in a rotationally fixed manner due to its geometry.

Preferably, the attachment may be sleeve-shaped with a cut or chamfered outer side, so that a planar abutment surface (D-shaped outer contour, in particular also D-shaped inner contour) is formed in sections on the radial outer side of the attachment. This planar abutment surface of the cut outer side preferably protrudes in the fixed position, in particular in sections as the outermost surface of the sterilization sieve basket, in the width and/or depth direction, wherein this abutment surface is preferably perpendicular to the sieve basket bottom (vertical). In particular, the abutment surface in the fixed position is parallel to the outer side of the sieve basket wall (in this area).

According to an aspect of the invention, the sterilization sieve basket may comprise at least one extension module of the sieve basket handle/sieve basket handle fitting, which comprises the bearing, in particular the joint, the sieve basket handle mounted or hinged in the bearing or joint, respectively, and an extension structure. The extension module of the sieve basket handle is provided and adapted to be attached/mounted/fastened to the at least one sieve basket wall, in particular via a screw connection, a riveted connection and/or a welded connection, as a separate and ready-assembled module by means of the extension structure in a form-fitting and/or material-fitting manner. In this way, the extension module of the sieve basket handle can be manufactured and replaced separately from the rest of the sterilization sieve basket. A material different from the sieve basket bottom and/or sieve basket wall may also be used. Preferably, the sieve basket bottom and the sieve basket wall are manufactured in one piece, e.g. deep-drawn, and only the extension modules of the sieve basket handles are attached to one or two opposite sieve basket side walls. Alternatively or additionally, the extension module of the sieve basket handle may also be force-fitted via a force-fit connection, for example if the extension structure is configured as a clamping part. In particular, the sterilization sieve basket may have the extension module of the sieve basket handle, in particular the same extension module of the sieve basket handle, on two opposite sides or respectively on two opposite sieve basket walls.

According to a further aspect of the invention, the sterilization sieve basket may have, at two opposite rim/edge portions, a respective inner sieve basket handle and an associated fixing portion and/or press-on portion or element, to be movable and/or deformable by the selected movement in opposite directions, respectively, outside of the sterilization sieve basket, in particular to protrude outward in the fixed position relative to the outer side of the sieve basket wall in two opposite directions. This has the advantage that the sterilization sieve basket only has, preferably projecting, exposed contact points or contact surfaces at defined points, i.e. the fixing portion and/or press-on portions or elements, and comes into contact with a container tray, for example. This minimizes wear of the remaining sterilization sieve basket and creates a defined force application at two opposite contact points in order to clamp the sterilization sieve basket, in particular in the container tray. Preferably, the two rotational axes of the sieve basket handles are parallel to each other. Preferably, the two sieve basket handles are identical components in order to simplify production.

In particular, the sieve basket bottom is rectangular in shape, in particular with rounded corners, and the circumferential sieve basket side walls extend along the edges of the sieve basket bottom and perpendicular thereto.

In particular, a joint to which the sieve basket handle is hinged to the sieve basket wall is configured in the form of a hinge. Preferably, a bent sheet (bent around the rotational axis) serves as a first part of the hinge fixed to the side wall and the rod-shaped, hinged bearing portion of the sieve basket handle with two bent portions adjoining on both sides, between which the bent sheet is enclosed, serves as a second part of the hinge (in the manner of a step).

Preferably, the sieve basket handle has a substantially trapezoidal contour, wherein a bent rod with in particular a circular cross-section forms this contour. A short base side forms the gripping portion, the long base side as bearing portion is hinged to the sieve basket wall via the connection web oriented at an angle to the gripping portion and has an offset in the area of the joint and/or in the area of the fixing portion and/or press-on portion or the element in order to space the fixing portion and/or press-on portion or the element perpendicular to the rotational axis.

Preferably, the sieve basket handle has two separate fixing portions and/or press-on portions or elements, in particular with two attachments, which are arranged between joints in the depth direction and have the same distance to each other in the depth direction as a distance to the adjacent joint. In particular, a distance between pivot joint-fixing portion-fixing portion-pivot joint (in this order) in the width and/or depth direction is the same in each case.

Preferably, the sterilization sieve basket has a fixing portion and/or press-on portion or element arranged centrally as seen in the depth direction on each of two opposite sieve basket walls. Alternatively, the sterilization sieve basket may also have diagonally opposite fixing portions and/or press-on portions or elements, each with offset fixing portions and/or press-on portions or element as seen in the depth direction. In particular, the sterilization sieve basket may have exactly two diagonally opposite fixing portions and/or press-on portions or elements at the rim portions, as seen in plan view. Preferably, the sieve basket handle is an identical component.

Preferably, the fixing portion and/or press-on portion may be a rod-shaped portion extending over at least 30%, preferably over 50%, of the depth of the sterilization sieve basket and in the direction of the depth.

Preferably, the sieve basket handle may have a camshaft portion/camshaft-like portion on which the fixing portions and/or press-on portions or elements are provided on one of its longitudinal axes and the hinged portions of the sieve basket handle are provided on the other longitudinal axis. Thus, in particular, only the fixing portions and/or press-on portions or elements protrude and recesses in the sieve basket wall can be minimized. In addition, attachments cannot be displaced along a longitudinal axis.

Preferably, the element may be a deformable element, in particular an elastic cushion, which preferably comprises elastomer as a material or even consists entirely of elastomer. Further preferably, the cushion may be a rubber pad or a silicone cushion. Particularly preferably, the silicone cushion may consist entirely of silicone (full silicone). Preferably, during a selected movement of the sieve basket handle, in particular during the movement from the carrying position to the fixed position, the deformable element may be deformed by a mechanism via targeted squeezing in a direction outside of the sieve basket. In particular, during its selected movement, the sieve basket handle may press on one side or location of the cushion due to its geometry and thus force the cushion into a different position in order to specifically deform the deformable element in the direction outside of the sterilization sieve basket.

According to an embodiment, the sieve basket handle may be supported on the sieve basket wall in such a way that it is movable translationally in one direction or along one axis, respectively. Preferably, the sieve basket handle may be supported on the sieve basket wall in such a way that it can perform a translatory movement in the vertical direction (height direction; up/down). In particular, the sieve basket handle, preferably the connection web, may have a stop cooperating with the associated bearing arrangement in order to limit the translatory movement in at least one direction. Preferably, the connection web has two stops in order to limit the translatory movement of the sieve basket handle between a first position, in particular a carrying position, and a second position, in particular a fixed position. A deformable, elastic cushion may be supported on the sieve basket wall, preferably in the area of a recess, which interacts with the sieve basket handle. The sterilization sieve basket is preferably configured in such a way that during a selected translatory movement of the sieve basket handle, the sieve basket handle presses/pushes on a predefined point of the elastic cushion and deforms this cushion against its elastic pretensioning force in the direction outside. In particular, the sieve basket handle is not in contact with the elastic cushion in the carrying position and is in direct contact with the elastic cushion in the fixed position. Preferably, the sieve basket handle is U-shaped with two portions extending parallel to each other as the connection webs (long sides of the U) and a gripping portion arranged between them (short side of the U). This U-shaped sieve basket handle preferably protrudes with its two parallel connection webs each through a guiding opening or elongated borehole in preferably the height direction or through two spaced but coaxial (guiding) openings or boreholes, so that a translational guidance of the handle (similar to a bolt) is formed. In particular, the elastic cushion is arranged in the same position as the connection web when viewed in the depth direction, but further outside the sieve basket when viewed in the width direction, so that when the sieve basket handle moves, in particular downward, the connection web presses directly on the elastic cushion and presses it outward due to the geometric arrangement. Preferably, the elastic cushion, in particular together with the bearing, may be at least partially enclosed by a housing with respect to the inner volume of the sieve basket, so as to protect the mechanism against disruptive influences, such as slipped instruments.

Seen in particular in longitudinal section, the elastic cushion has a triangle as its basic shape, preferably with rounded corners. This triangular shape forms the base of a block which extends in particular in the depth direction of the sieve basket. In particular, the elastic cushion is attached, held or supported on the sieve basket wall in such a way that, in a non-deformed state, one (for example long) side or side surface of the triangular cushion is arranged in the direction of the height and/or parallel to the associated sieve basket side wall portion. In this way, in a non-deformed state, the sieve basket can be easily inserted into a container tray. If the handle is displaced via the selected movement, the connection web subsequently presses on the other, inclined side of the triangular cushion, which serves as a kind of ramp, thereby forcing the cushion, which in particular is attached to the inner wall of the sieve basket at its upper end, outward. In this process, the cushion is elastically twisted and deformed about an axis in the depth direction. If the handle with the connection web(s) is moved upward again, the contact pressure is released again and the cushion deforms back to its original, non-deformed state. Alternatively, the cushion may be mounted to rotate about an axis and move back inward to its original state via gravity.

Preferably, the bearing is a formed sheet metal component with at least two parallel sheet portions which extend in the width and depth directions and each have coaxial and in particular congruent openings or boreholes, in particular with an opening axis in the height direction, so that a connection web of the handle can be moved translationally in these (guide) openings. Preferably, the opening is not rotationally symmetrical in order to prevent twisting and jamming and to allow, for example, a stop.

The object of the invention is solved with respect to a generic sterilization sieve basket system according to the invention in that the sterilization sieve basket system comprises a sterilization sieve basket lid and a sterilization sieve basket according to the invention. In particular, the sterilization sieve basket lid may have a substantially plate-like or grid-like basic shape defining an upper side, and may preferably be adapted to the sterilization sieve basket so as to provide a closure mechanism together with the sieve basket handles.

The object of the invention with respect to a generic container system is solved according to the invention in that the container system comprises a container/sterile container and a sterilization sieve basket according to the invention. The sterile container, which may also be any conventional or respectively known container, has a container tray and may further preferably have a container lid matching the container tray in order to delimit an inner volume of the container from an environment. Furthermore, the sterile container may comprise a filter on the side of the container tray and/or on the side of the container lid. The sterilization sieve basket is in particular adapted to be insertable into the container tray of the container, wherein the fixing portion and/or press-on portion or element in the fixed position directly abuts (is in contact with) the inner wall of the container tray and braces the sterilization sieve basket against the container tray (in at least one direction) and thus positionally fixes and secures the sterilization sieve basket in the container. The sterilization sieve basket therefore has smaller outer dimensions than the inner dimensions of the container tray in order to be inserted into the latter. In particular, this creates a (small) gap circumferentially between the inner wall of the container tray and the side wall of the sterilization sieve basket, which would allow movement of the sterilization sieve basket in the container tray. However, if the sieve basket handle(s) is/are now moved selectively, the fixing portions and/or press-on portions or elements move and/or deform in the direction outside of the sterilization sieve basket and subsequently in the direction toward the container tray and directly contacts/contact the inner wall of the sterile container due to the operative connection with the fixing portion(s) and/or press-on portion(s) or element(s). If, for example, a sieve basket handle is provided on two opposite rim portions of the sieve basket wall, these together with the fixing portions and/or press-on portions or elements spread the sterilization sieve basket against the opposite inner walls of the container tray and fix it in the container. The container tray and the sterilization sieve basket are thus geometrically matched to each other in such a way that this spreading, pressing-on or clamping function is realized.

BRIEF DESCRIPTION OF THE DRAWINGS

The present invention is explained in more detail below based on preferred embodiments with reference to the accompanying figures. The following is shown.

The figures are schematic in nature and are intended only to aid understanding of the invention. Identical elements are provided with the same reference signs. The features of the various embodiments can be interchanged.

DETAILED DESCRIPTION

Figure 1:
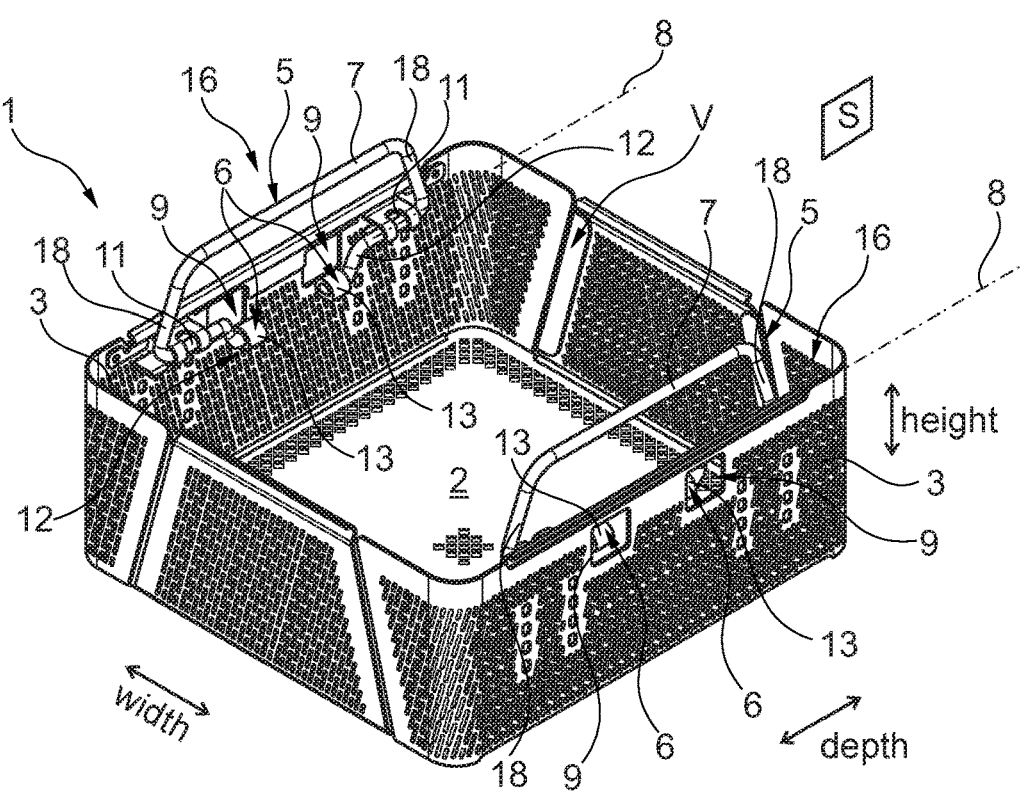
FIG. 1 shows a perspective view of a sterilization sieve basket according to the invention in accordance with a preferred embodiment, in which both sieve basket handles are in the carrying position.
Figure 2:
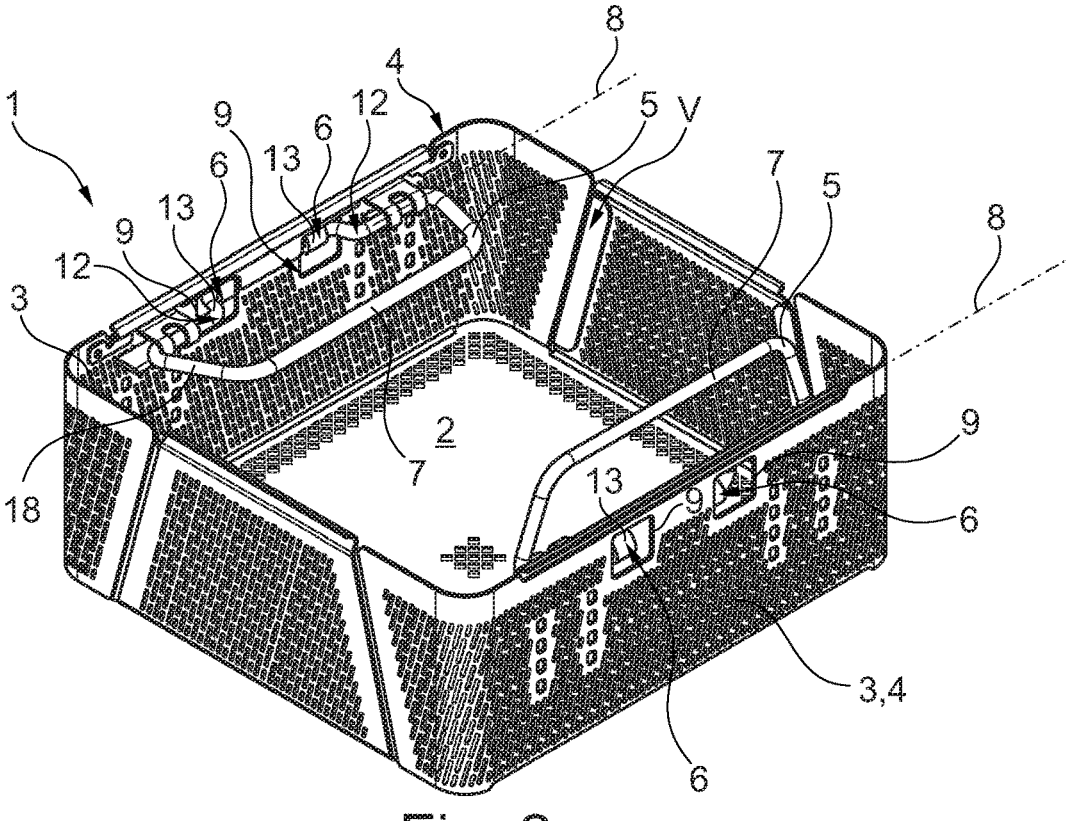
FIGS. 2 and 3 show a perspective view of the sterilization sieve basket of FIG. 1, in which one of the two sieve basket handles has been pivoted to the fixed position by a selected movement.
Figure 3:
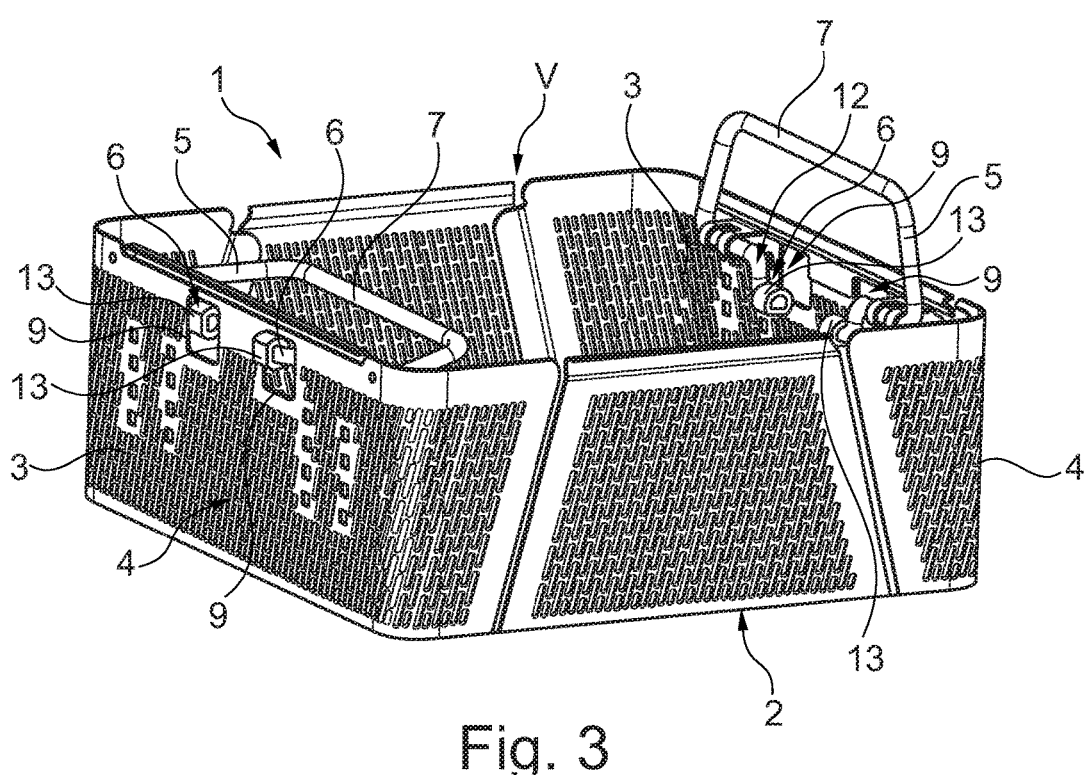
Figure 4:
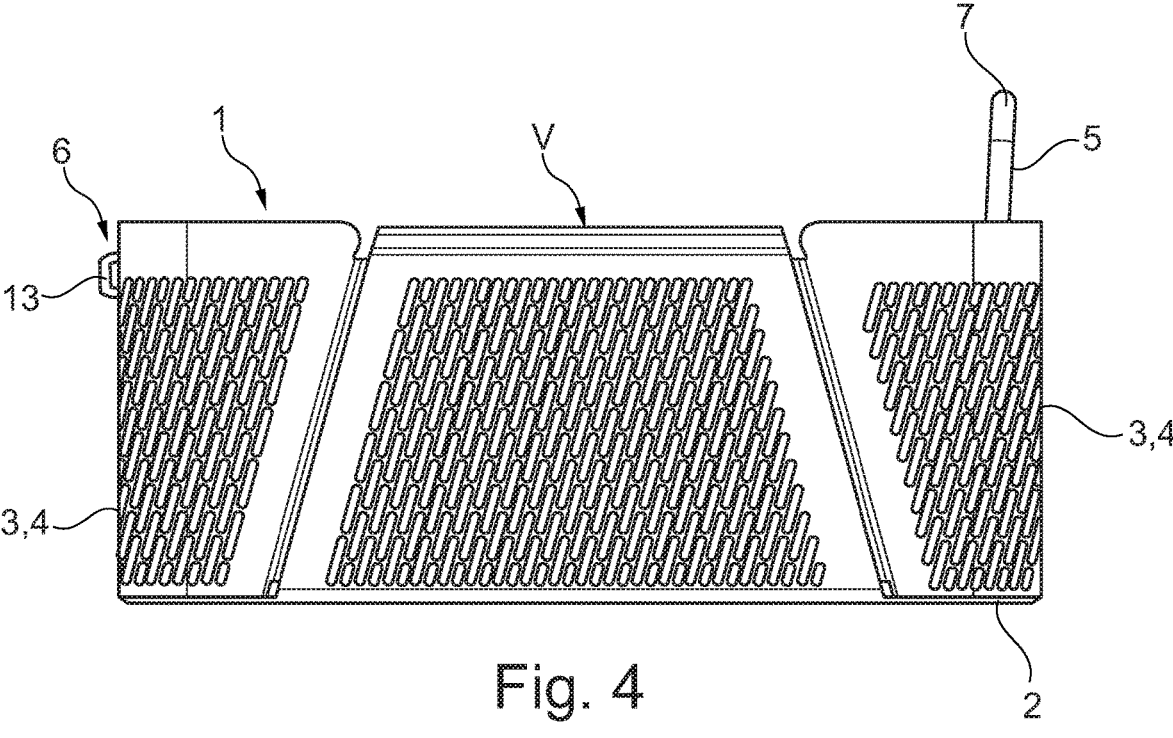
FIG. 4 shows a front view of the sterilization sieve basket from FIGS. 1 to 3.
Figure 5:
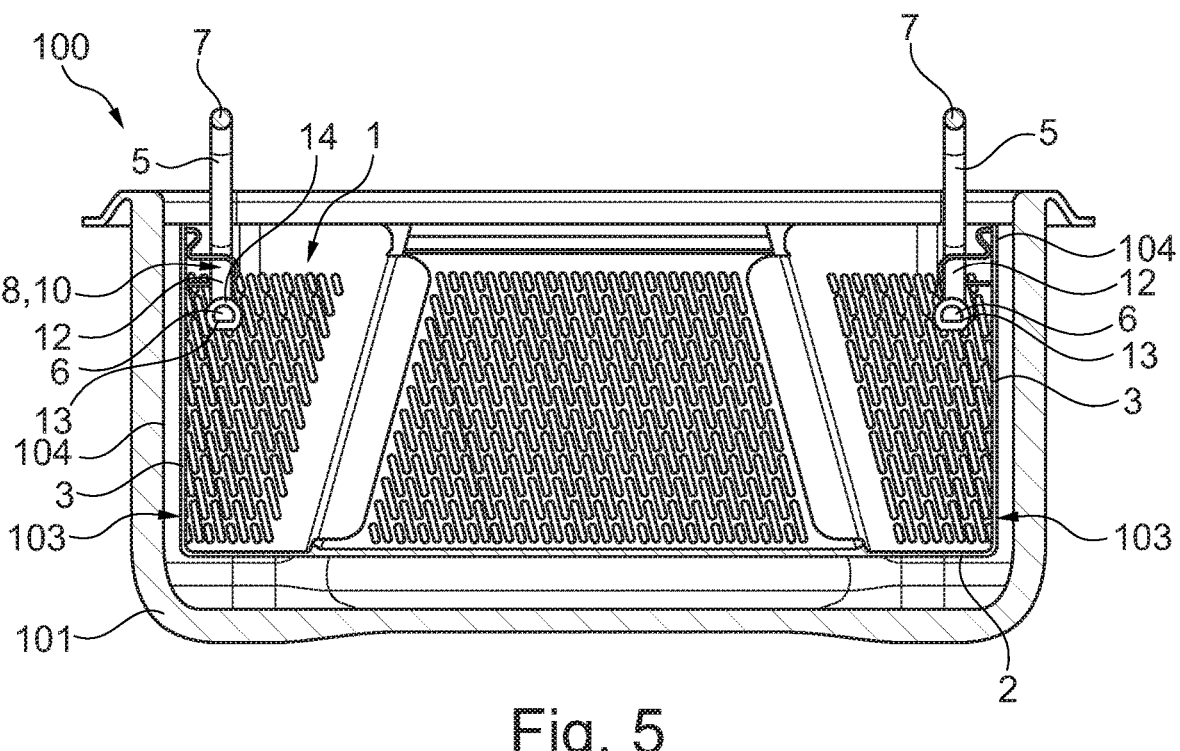
FIG. 5 shows a longitudinal sectional view of the sterilization sieve basket from FIGS. 1 to 4, which is used in a sterile container system according to the invention in accordance with a preferred embodiment, wherein both sieve basket handles are in the carrying position.
Figure 6:
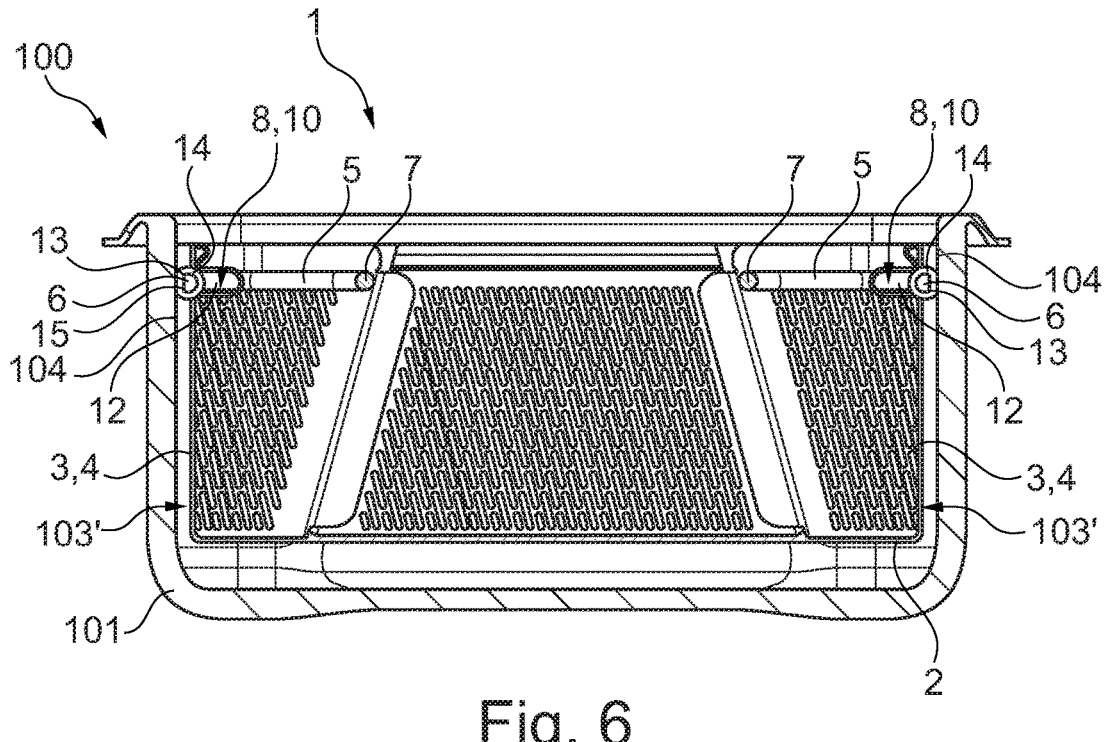
FIG. 6 shows a longitudinal sectional view of the sterilization sieve basket and of the sterile container system from FIG. 5, wherein both sieve basket handles are in the fixed position.
Figure 7:
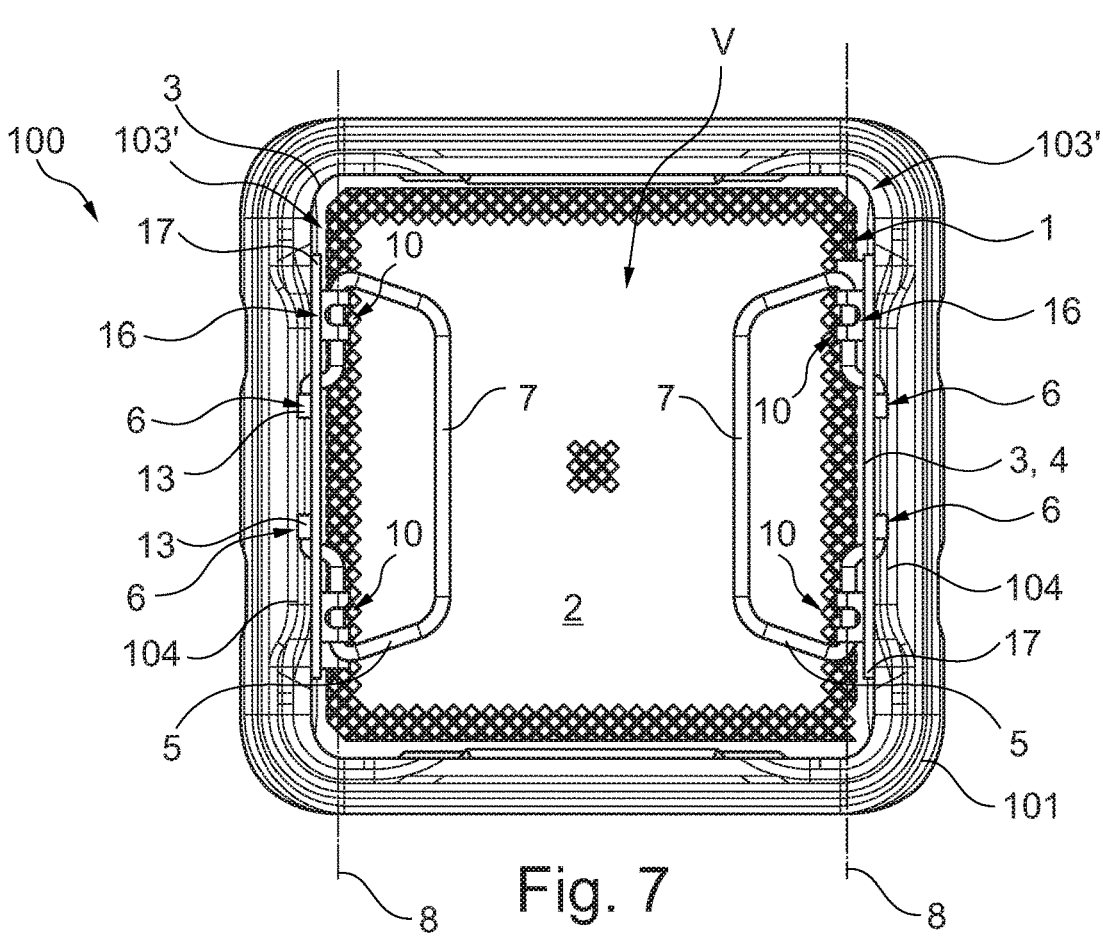
FIG. 7 shows a top view of the sterilization sieve basket and sterile container system from FIG. 6, FIGS. 8 and 9 show a perspective partial view of a sterilization sieve basket in accordance with a further preferred embodiment.

FIGS. 1 to 7 show a sterilization sieve basket 1 (hereinafter referred to only as sieve basket) according to the invention in accordance with a first preferred embodiment, which is provided and configured for insertion into and removal from a container system and is inserted or insertable in the 30 (sterile) container system 100 according to the invention in a preferred embodiment (see FIGS. 5 to 7).

The sieve basket 1 has a flat/planar, grid-shaped, square sieve basket bottom 2 with rounded corners, which is fully enclosed by four grid shaped sieve basket walls 3 of circumferentially equal height extending perpendicular to the sieve basket bottom 2. The sieve basket bottom 2 and the sieve basket walls 3 define an inner volume V of the sieve basket or of a sieve basket interior, respectively, in which, for example, medical or surgical instruments can be accommodated and arranged for sterilization.

The sterilization sieve basket 2 furthermore has two pivotable, arched sieve basket handles 5 lying on the inside of opposite upper rim portions of the sieve basket wall 3, which can each be pivoted independently of each other into at least one carrying position/carrying state and into a fixed position/fixed state. Each of the two sieve basket handles 5 has a gripping portion 7, which is connected to a bearing portion/hinged area 11 of the sieve basket handle 7 via a connection web 18 oriented at an angle to the gripping portion 7.

According to the invention, the sieve basket 1 has on each of the two sieve basket handles 5 (hereinafter referred to as handle), an operatively connected/coupled and movable, in particular pivotable, fixing portion 6 spaced from the gripping portion 7, which is movable and/or deformable by the selected movement of the handle 5 from the sieve basket side wall 3 in the direction outside of the sieve basket 1.

In this embodiment, the fixing portion 6 in the carrying position is arranged in the inner volume V of sieve basket and does not protrude from an outer side 4 of the sieve basket wall 3, wherein during the selected movement of the handle 5 from the carrying position to the fixed position, the fixing portion 6 is moved in the direction outside of the sterilization sieve basket and in the fixed position of the handle 5 protrudes outward from the outer side 4 of the sieve basket wall 3 in order to abut there. Specifically, in this embodiment, the two handles 5 are identical components and are each configured as a two-sided lever that, in addition to the (pivotable) gripping portion 7 for manually gripping the handle 5, also has the fixing portion 6 as a structural portion and is pivotable about a rotational axis 8.

Thus, a structural portion of the one-piece handle 5, i.e., the fixing portion 6, is configured such that in the carrying position, in which the arched handles 5 are substantially vertical in height and can be easily grasped manually from above by a user for removing and inserting the sieve basket 1, the fixing portion 6 is located in the inner volume of the sieve basket and does not protrude from the associated sieve basket wall 3 or the outer surface 4. In an inserted state, in which the sieve basket 1 is inserted in a container tray 101, a circumferential gap 103 is formed between the inner walls 104 of the container tray 101 and the side walls 3 or respectively the outer surfaces 4 defined by them (see FIGS. 5 to 7). This circumferential gap 103 allows good handling of the sieve basket 1, in particular easy removal and displacement, but also displacement of the sieve basket 1 in the width and depth direction.

If now one handle 5 (see FIG. 2 left side) or respectively both handles 5 (see FIGS. 6, 7) are pivoted about the rotational axis 8 by the selected movement from the carrying position to the fixed position, the two-sided lever configuration of the handle 5 causes the gripping portion 7 to be pivoted inward into the sieve basket volume V, while at the same time and in the same direction the fixing portion 6 opposite the gripping portion 7 is pivoted about the rotational axis 8 out of a recess 9 in the associated sieve basket wall 3 from the sieve basket wall 3 in the direction outside of the sieve basket 1 and protrudes with respect the outer side 4 (in the width direction). In this way, a dimension or distance between the two outer sides 4 facing away from each other or two opposite sieve basket walls 3 is increased, as it were. This has the effect that the previously fully circumferential gap 103 is no longer fully circumferential, but in a manner of speaking as an interrupted gap 103'. In the fixed position, the fixing portions 6 interrupt the gap 103' and lie directly against or contact an inner wall 104 of the container tray 101.

In the fixed position, the sieve basket 1 is thus fixed and secured in the container tray 101 in at least one direction, in this case the width direction (parallel to the sieve basket bottom 3), via the (variable) increased width by the opposite fixing portions 6, as explained in detail below. This configuration of the sieve basket 1 according to the invention prevents slipping in the container 101, 102 and provides a simple and efficient transport protection as well as scratch protection. Furthermore, good handling of the sieve basket 1 is ensured and the sieve basket 1 can be easily inserted into the container tray 101 in the carrying position and can also be removed again. Switching between a handling state and a fixed state is carried out in a particularly simple manner.

The fixing portion 6 is arranged between the two hinged areas 11 as seen in the depth direction. Alternatively, the fixing portion may of course also be arranged outside or respectively to the outside of the hinged areas 11 as viewed in the depth direction.

The plane, vertical and grid-shaped sieve basket wall 3 on each of the four sides/edges of the sieve basket bottom 2 and each with an arcuate transition (rounded corner edge) at the corners, defines an outer side/outer surface 4 facing away from the inner volume V of sieve basket or the sieve basket bottom 2 or, in this embodiment, four outer surfaces 4 with two times two outer surfaces 4 facing away from each other (of the two sieve basket walls 3 facing each other), which delimits the sterilization sieve basket 1 from the surroundings to the sides. As shown in particular in FIG. 4, the outer surfaces 4 facing away from each other each form a plane parallel to each other, both extending perpendicular to the sieve basket bottom 2 in height and along the sieve basket bottom 2 in depth.

In the first embodiment of FIGS. 1 to 7, the sieve basket 1 is symmetrical to a vertical (first) symmetry plane S, wherein a sieve basket handle 5 is provided on each side. In the following, it is therefore sufficient if only one side of the sterilization sieve basket 1 is described in detail. Furthermore, in the first embodiment, the sieve basket 1 is even symmetrical to a further vertical symmetry plane which is perpendicular to the first symmetry plane S. The sieve basket 1 thus has four (mirror) symmetrical quarters.

The arched handles 5 on the inside of the basket on two opposite side surfaces of the side wall 3 are hinged via a pivot joint 10 in the manner of a hinge so as to be rotatable or pivotable about the rotational axis 8. The rotational axis 8 is parallel to the outer surface 4 of the sieve basket wall 3 and to the sieve basket bottom 2. The handles 5 can thus be pivoted from a substantially vertically upward-pointing carrying position/gripping position/unfolding position inward into the inner volume V of the sieve basket or vice versa. The arched handles 5 are hinged to an upper portion of the associated sieve basket wall 3 in the pivot joint 10 facing away from the sieve basket bottom 2 and as seen in FIGS. 1 to 7.

The handle 5 is a formed cylindrical metal rod with a circular cross-section. As a result of the forming process, the metal rod now forms an essentially trapezoidal contour. The short base side of the trapezoid forms the rod-shaped/cylindrical gripping portion 7, which always extends in the direction of the depth of the sieve basket 1 (i.e. always parallel to the sieve basket bottom 2 in all positions/states). The long base side of the trapezoid is hinged near the two short connection webs 18 as legs and interrupted in the middle. Specifically, the hinged, rod-shaped area/bearing portion 11 of the long base edge is formed parallel to the gripping portion 7 and makes a Z-shaped or step-shaped portion/kinking/offset 12 away from the gripping portion 7 and the rotational axis 8 respectively after this area. This step-shaped portion 12 thus has two parallel rod-shaped portions (the hinged area 11 and the fixing portion 6) and an oblique portion arranged between them. The terminal portion of the step-shaped portion 12, which is parallel to the gripping portion 7, to the rotational axis 8 and to the sieve basket bottom 2, forms the fixing portion 6 of the handle 5.

Due to the step-shaped portion 12, the fixing portion 6 is spaced perpendicular to the rotational axis 8 and forms the second side of the two-sided lever. The entire handle 5 is formed or, respectively, the rod as the handle 5 is formed so that it lies in one plane. As also shown in the longitudinal section view in FIG. 5, the handle 5 forms a straight two-sided lever (a straight line between the fixing portion 6, the rotational axis 8 and the gripping portion 7, in this order, as seen in a longitudinal section in the width/height direction) with an arrangement that is only offset in depth (different depth positions). In other words, in extension of the connection of the gripping portion 7 and the rotational axis 8, the fixing portion 6 is formed on the other side with respect to the rotational axis 8. In this embodiment, a perpendicular (shortest) distance between the gripping portion 7 and the rotational axis 8 for a lever action is approximately four times greater than a perpendicular distance between the rotational axis 8 and the fixing portion 6.

An attachment 13 made of silicone, in particular foam silicone, with inherent elasticity is attached to the fixing portion 6. The attachment 13 compensates for tolerances between the inner wall 104 of the container tray 101 and the fixing portions 6. The attachment 13 is sleeve-shaped with a flattened, planar (radial) inner and outer side (D-shaped). Similarly, the rod-shaped handle 5 of the fixing portion 6 is ground flat on a side facing away from the gripping portion 7, so that it also has a D-shaped outer contour 14. The D-shaped, sleeve-shaped attachment 13 is plugged onto the matching, complementary, D-shaped plug-on portion, thus locking the rotational degree of freedom of the attachment 13. Moreover, in the fixed position, the attachment 13 respectively forms a perpendicular, planar abutment surface/fixation surface 15 parallel to the outer side 4 of the associated sieve basket walls 3 in order to lie flat against the inner wall 104. The coefficient of friction with the inner wall 104 is increased by the silicone attachment 13. The attachment 13 can also be easily replaced as a wearing part.

In this embodiment, each of the two handles 5 has two fixing portions 6 at the same perpendicular distance from the rotational axis 8, which are arranged between the pivot joints 10 as seen in the depth direction. Each of the four fixing portions 6 has a respective associated recess 9 in the form of a square opening in the sieve basket wall 3. If the handle 5 is pivoted into the fixed position by the selected movement, the fixing portions 6 with the attachments 13 each protrude through the recesses 9 in the width direction with respect to the outer side 4 in two opposite directions and form the largest dimension of the sieve basket 1 (see FIG. 7). The fixing portions 6 thus clamp the sterilization sieve basket 1 in the container tray 101 in the width direction. The attachments 13 made of silicone with the associated high coefficient of friction and abutment surface 15 also achieve fixation in the depth direction as well as in the height direction.

Both the sieve basket bottom 2 and the sieve basket wall 3 have a large number of square openings and longitudinal slots punched out in order to establish a fluid connection between the inner side and the outer side 4 and thus make the outer side 4 penetrable, in particular for water vapor. The material of the sieve basket bottom 2 and the sieve basket wall 3 is aluminum and/or stainless steel.

In this embodiment, the sieve basket 1 has an extension module 16 of the sieve basket handle with an extension structure 17. The extension module 16 of the sieve basket handle with the pivot joint 10, the handle 5 and the extension structure is manufactured as a separate module and then riveted to the remaining sieve basket 1, i.e. the sieve basket bottom 2 and the sieve basket wall 3. The pivot joint 10 is configured in each case as a plate bent around the rotational axis 8, through which the hinged area 11 of the handle 5 protrudes. The extension module 16 of the sieve basket handle can be configured, for example, with different materials to the rest of the sieve basket 1 and can be assembled separately in advance, which improves a production process.

Figure 8:
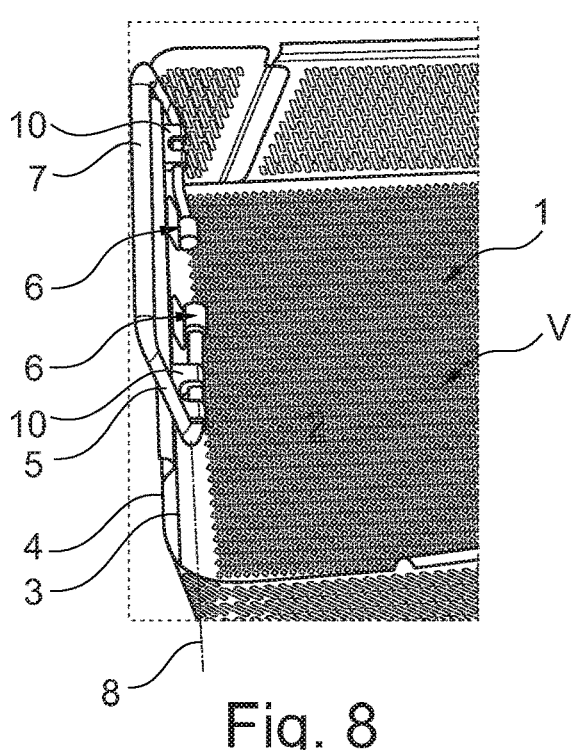
Figure 9:
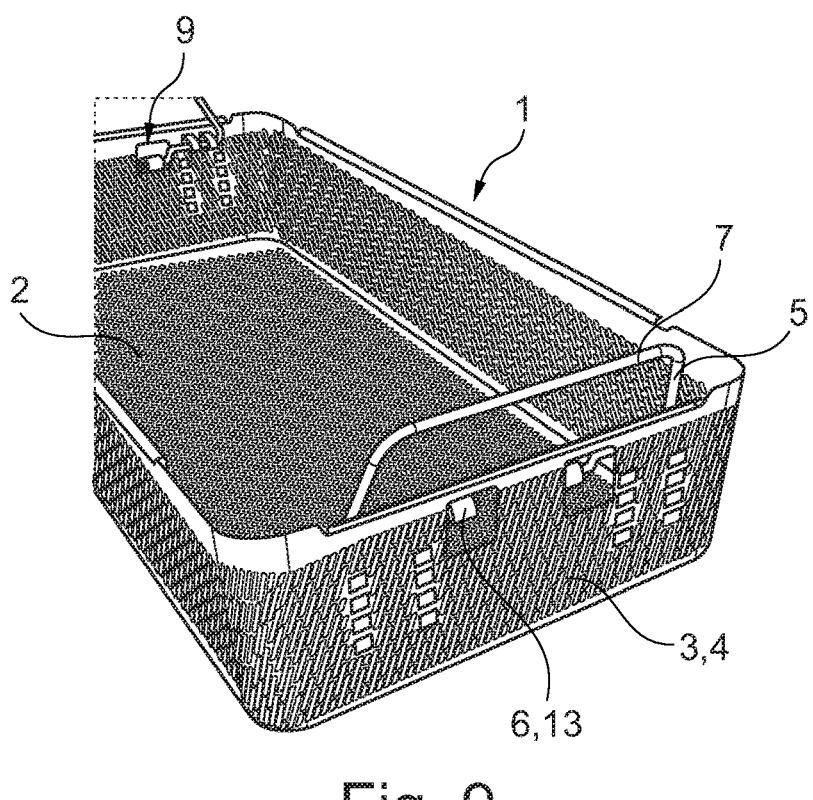
Figure 10:
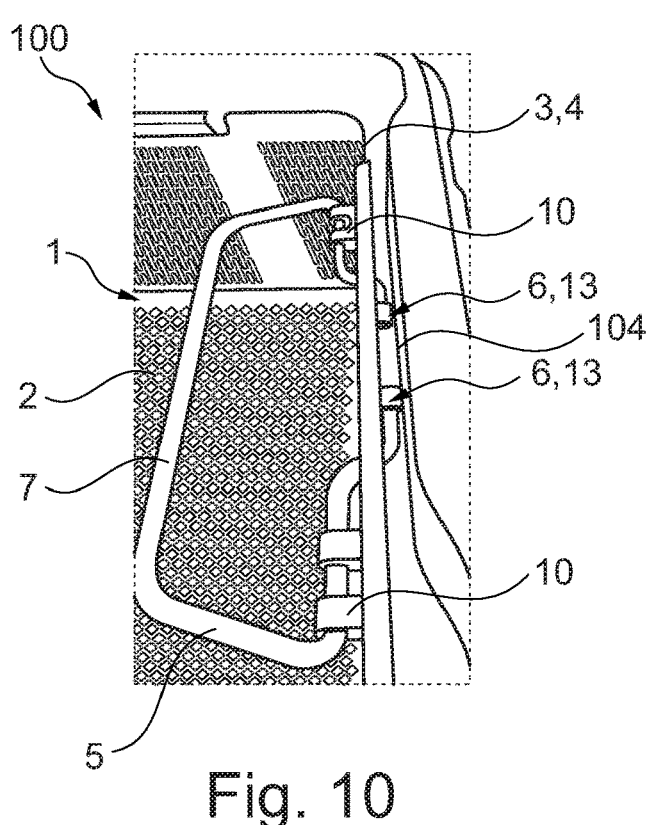
FIG. 10 shows a perspective partial view of the sterilization sieve basket from FIGS. 8 and 9, which is inserted in a container tray and in which a sieve basket handle is in the fixed position.

FIGS. 8 to 10 show a further, second preferred embodiment of the screen basket 1 with a rectangular sieve basket bottom 2.

Figure 11:
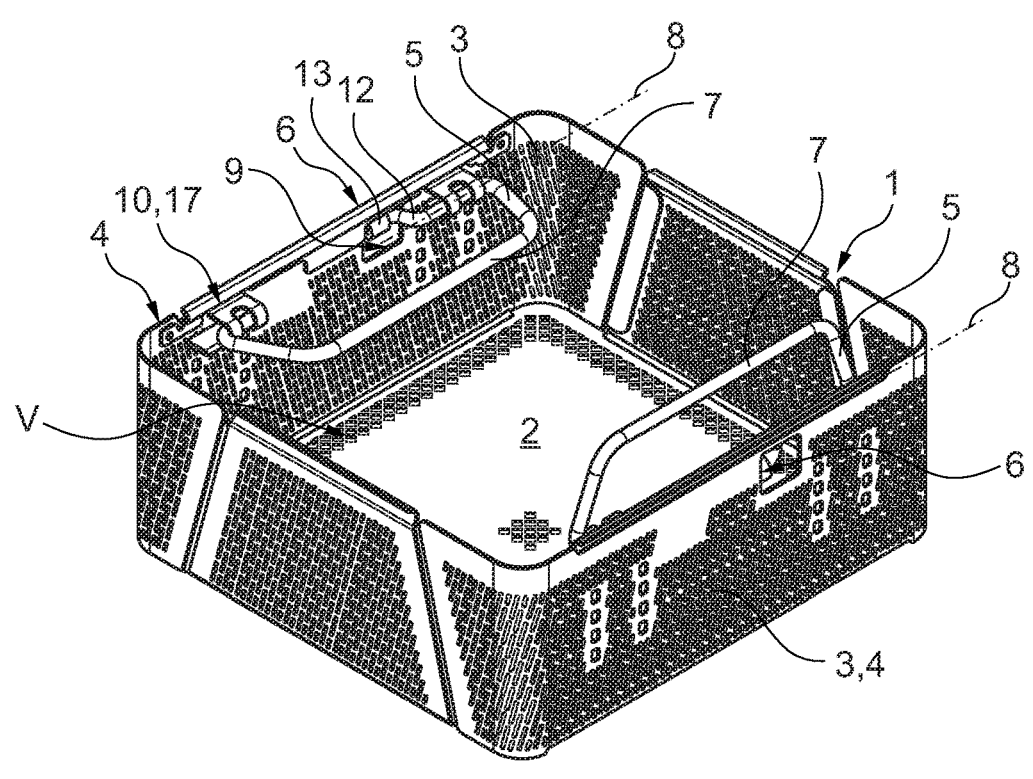
FIG. 11 shows a perspective partial view of a sterilization sieve basket according to the invention of a further preferred embodiment in which one fixing portion per side is provided.

FIG. 11 shows a further, third preferred embodiment of the sieve basket 1. The two handles 5 provided on opposite sieve basket walls 3 are identical components. In contrast to the first embodiment, however, only one fixing portion 6 is formed on each handle 5. The second step-shaped portion with the associated fixing portion is omitted. The one fixing portion 6 is not arranged in the center of the handle 5 as seen in the depth direction, but offset from the center. Only one of the associated square openings is respectively provided as recess 9 in the sieve basket wall 3. Both fixing portions 6 are in the same position in the depth direction.

Figure 12:
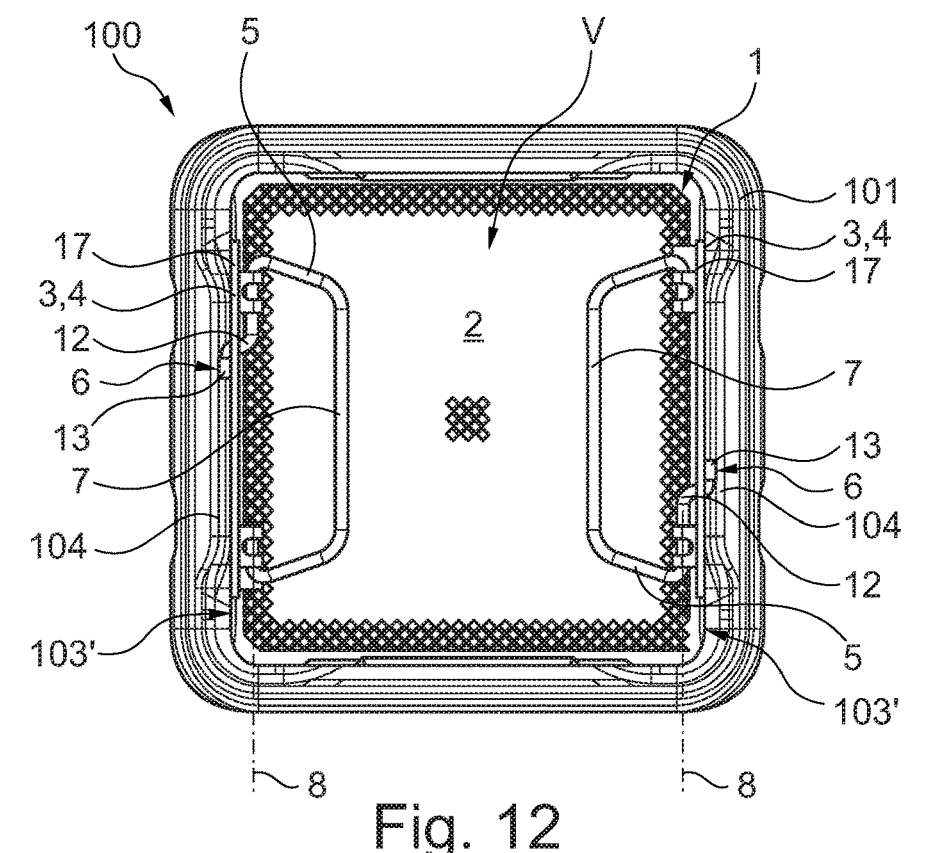
FIG. 12 shows a top view of the sterilization sieve basket of a further preferred embodiment, which is inserted in a container tray and in which the sieve basket handles are in the fixed position, and which has one fixing portion per side, which are arranged diagonally.

FIG. 12 shows a further, fourth preferred embodiment of the sieve basket 1 and a container system 100 with two diagonally opposite fixing portions 6. Both handles 5 are again of the same shape and are provided on opposite sieve basket walls 3. The handle 5 is the same as from the embodiment of FIG. 11, with the difference that one handle 5 has been rotated 180° about a vertical axis and was then hinged to the sieve basket wall 3 so that the fixing portions 6 and the recesses 9 are diagonally opposite each other in a plan view as in FIG. 12.

Figure 13:
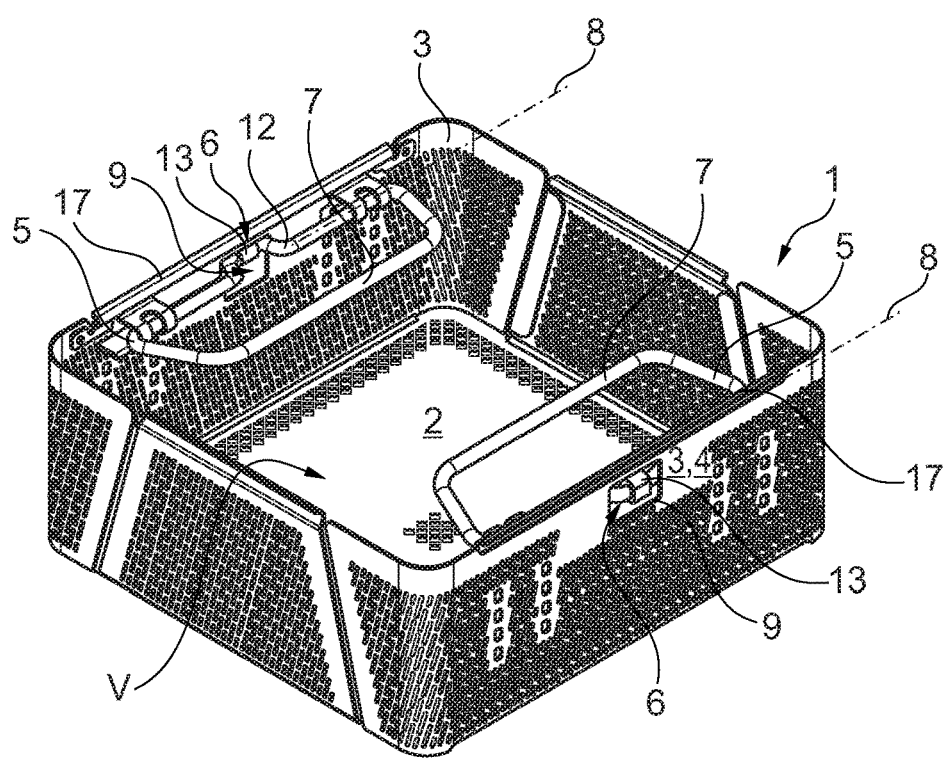
FIG. 13 shows a perspective view of a sterilization sieve basket according to the invention of a further preferred embodiment, with a central fixing portion per side.

FIG. 13 shows a further, fifth preferred embodiment of the sieve basket 1, in which the arched, trapezoidal handle 5 now has a continuous, rod-shaped configuration on its long base side and only a central, rod-shaped portion as step-shaped portion 12 thereof is set back from the rotational axis 8 relative to the gripping portion 7, similar to a bulge. The central portion as fixing portion 6 again has the attachment 13, which can be clipped or molded on.

Figure 14:
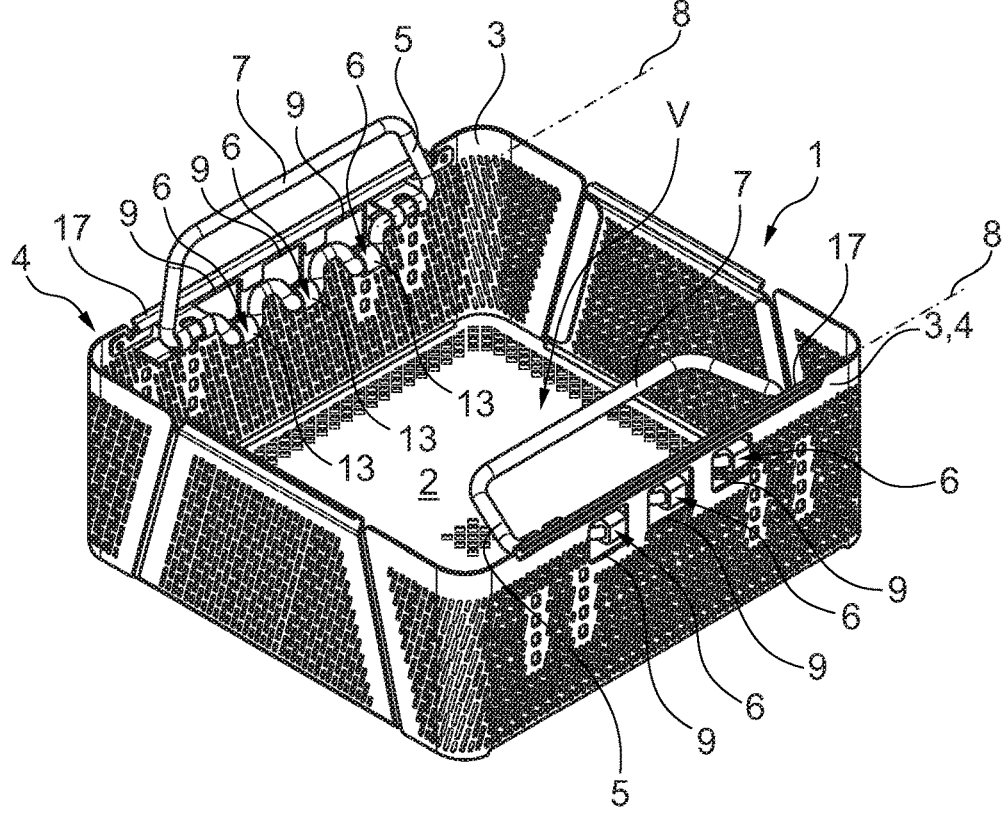
FIG. 14 shows a perspective view of a sterilization sieve basket according to the invention of a further preferred embodiment, which has multiple, here three, fixing portions per side.

FIG. 14 shows a further, sixth preferred embodiment of the sieve basket 1, in which each handle 5 has three fixing portions 6 equally distributed as seen in the depth direction, each with attachments 13 and the same perpendicular distance from the rotational axis 8. The sieve basket 1 has three complementary square openings as recesses 9 on the two opposite sieve basket walls 3. The long base side of the trapezoidal, arched handle 5 has a camshaft-like configuration with three step-shaped portions 12.

Figure 15:
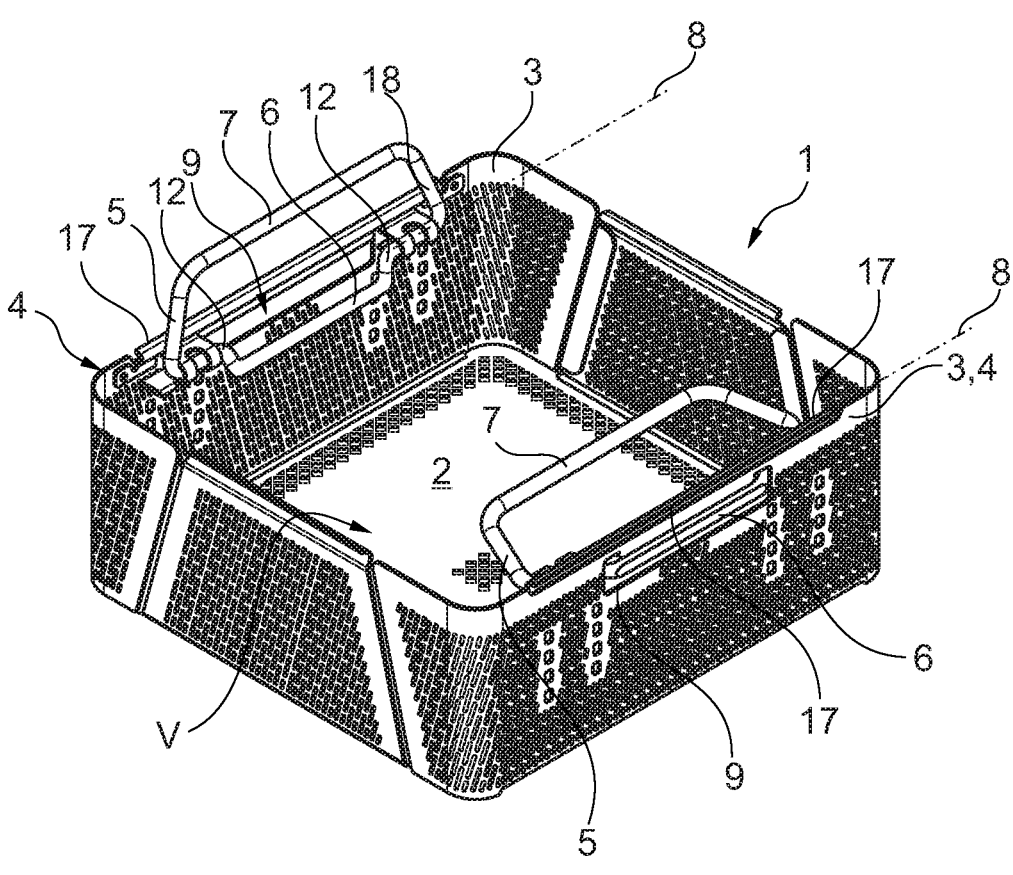
FIG. 15 shows a perspective view of a sterilization sieve basket according to the invention of a further preferred embodiment with a rod-shaped fixing portion on each side.

FIG. 15 shows a further, seventh preferred embodiment of the sieve basket 1, which has two opposite handles 5 without attachment. The long base side of the trapezoidal and arched handles 5 is made continuous and is set back from the rotational axis 8 by two step-shaped portions 12, each starting directly next to the two pivot joints 10. Alternatively, it can also be said that the hinged area 11 of the handle is offset from the long base side of the trapezoid toward the short base side. The long rod-shaped section between the hinged areas 11 forms the fixing portion 6. In this embodiment, the two opposite recesses 9 in the sieve basket walls 3 are configured as an elongated rectangular opening in the depth direction, which extends approximately 50% of the depth of the sieve basket 1. On the long, rod-shaped fixing portion 6 projecting in the fixed position, a vertical plane abutment surface 15 is provided on the outside in the width direction, so that the fixing portion 6 has a D-shaped contour. The plane abutment surface 15 is parallel to the respective outer side 4 in the fixed position and forms the outermost, elongated (contact) surface on the upper rim section of the sieve basket 1, as seen in the width direction.

Figure 16:
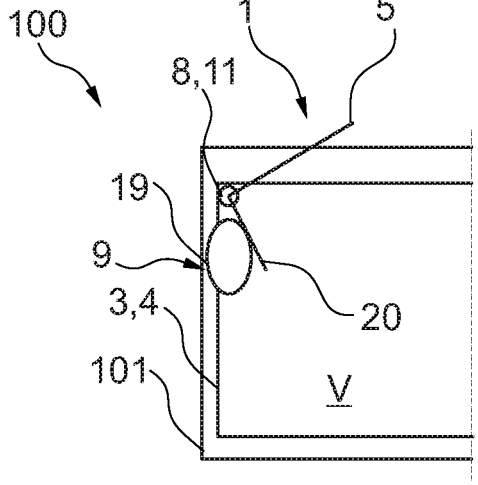
FIG. 16 shows a schematic, longitudinal, sectional, partial view of a sterilization sieve basket according to the invention and a sterile container system of a further preferred embodiment, with an elastic cushion.
Figure 17:
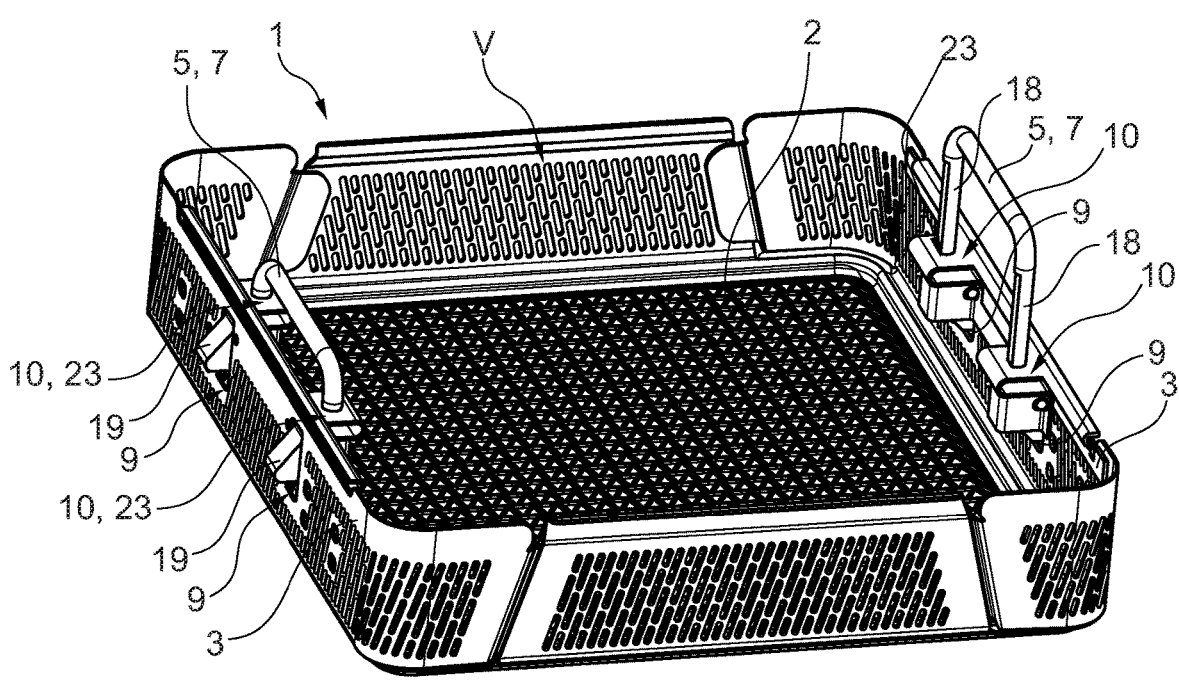
FIG. 17 shows a perspective view of a sterilization sieve basket according to the invention of a further preferred embodiment.
Figure 18:
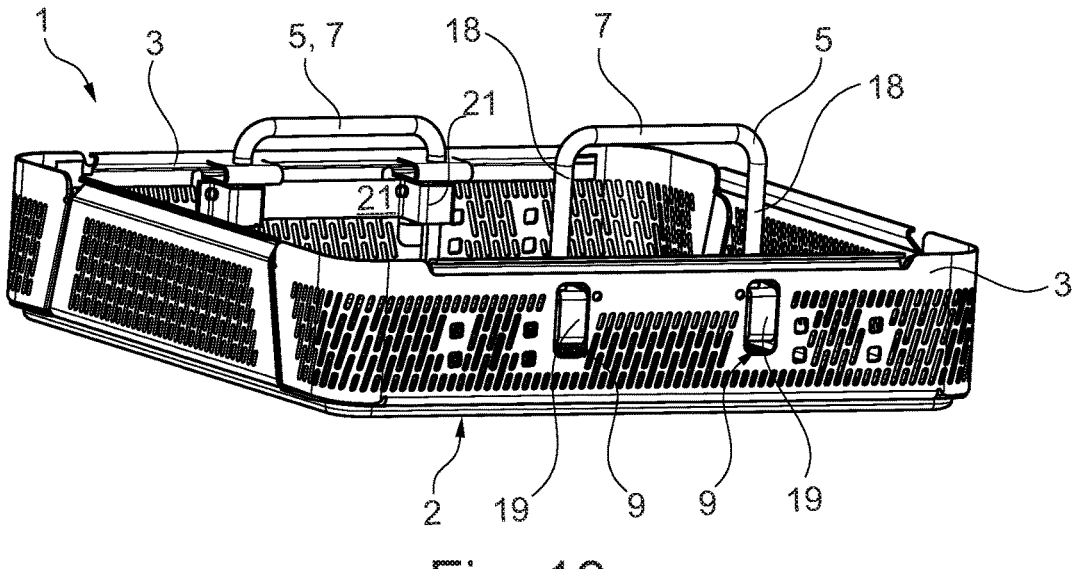
FIG. 18 shows a further perspective view of the sterilization sieve basket from FIG. 17.
Figures 19, 20:
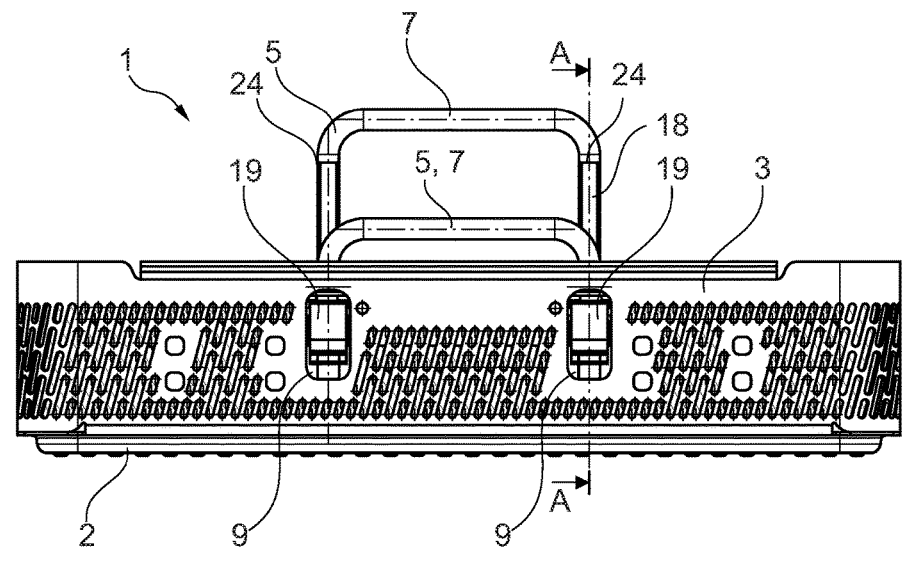
FIG. 19 shows a side view of the sterilization sieve basket from FIGS. 17 and 18.
FIG. 20 shows a longitudinal sectional view of the sterilization sieve basket from FIGS. 17 to 19.

FIG. 16 shows in a schematic, longitudinal, sectional, partial view a further, seventh preferred embodiment of a sieve basket 1 according to the invention, which has, as fixing portion and/or press-on portion or element, an elastic cushion, in this case a rubber pad 19, which deforms outward during a selected movement of the sieve basket handle 5 from the carrying position into the fixed position by a mechanism via targeted squeezing. The rubber pad 19 is fixed to the sieve basket side wall 3 and in the fixed position protrudes in sections toward the container tray 101 through the recess 9 opposite the outer side 4. As a mechanism, it is provided in the present case that the handle 5 as a two-sided, L-shaped lever has a squeeze arm 20 angled at 90°, which in the fixed position points inward or downward into the sieve basket 1. During the selected movement of the handle 5 into the fixed position, the squeeze arm 20 presses on one side/site of the rubber pad 19 due to the geometry, in order to build up pressure during continuous selected movement of the handle 5 and thus to deform the rubber pad 19 specifically in the direction outside toward the container tray 101 in order to lie there. In particular, the sieve basket 1 is configured to fix the handle 5 in the fixed position. The deformation in the direction outside causes the sieve basket 1 to be braced in the container tray 101 in the width direction.

FIGS. 17 to 20 show a further, eighth preferred embodiment of sieve basket 1, in which elastic solid silicone cushions 19 are provided as fixing elements. The (inverted) U-shaped handle 5 is translationally mounted on the inner wall of the sieve basket on two bearings 10 and can be pushed upward into the carrying position and downward into the fixed position. The bearing 10 is in the form of a formed sheet metal component with two sheet portions 22 arranged parallel to each other, in which coaxial and congruent guiding openings 23 are formed, the common axis of which extends in the direction of the height. Each guiding opening 23 has a circular contour with a cut-off side or, respectively, an opening contour with a straight base side and an adjoining semi-circular arc. One connection web 18 of the handle 5 projects into each (two) guiding opening 23. The U-shaped handle 5 in the form of a bent, cylindrical rod has a circular cross-section, wherein a chamfer or straight, planar milling is provided along the longitudinal axis of the so-called running sections of the connection webs 18 (sections that are guided in the bearing 10 and interact with it) complementary to the guiding opening 23. This configuration results in a stop 24 above and below the chamfer respectively (circular cross-section protrudes with respect to the chamfered running section) so that the sliding movement of the handle between the carrying position and the fixed position is limited. It can also be said that the handle 5 can execute a linear movement via the connection webs 18 and the guiding openings in the manner of slidingly mounted bolts.

Furthermore, the cushions 19 are arranged on the inner wall of the screen basket at the same depth as the associated connection web 18, but further outside of the screen basket 1, as seen in the width direction. The cushions 19 are attached to a housing 21 provided on the inner wall side of the sieve basket at their respective upper sections. The housing 21 encloses the mechanism and delimits it from the inner volume V. It is crucial that the cushions 19 are firmly connected (i.e. locally fixed) at their upper end to the housing 21 and thus to the sieve basket side wall 3. In a front view or longitudinal section view, as shown in particular in FIG. 20, the cushions 19 have a triangular basic shape and extend block-like in the depth direction. In a non-deformed state (handle 5 is pulled up into the carrying position; see right side in FIGS. 17, 18), one of the three side surfaces of the respective cushion 19 already protrudes through the recess 9 and thus slightly opposite the sieve basket wall 3 and extends parallel to the sieve basket wall 3. In an alternative embodiment not shown, this side surface may also be arranged flush with the sieve basket side wall 3 or inside the sieve basket 1 and not protrude.

If the handle 5 is now pushed from the carrying position (see right side FIG. 17, 18) into the fixed position (see left side FIG. 17, 18), a lower free end of the connection web 18 will collide with a (different) slanted side of the corresponding triangular (wedge-shaped) cushion 19 during this selected movement. This inclined side serves as a kind of ramp and, as a result of the movement, displaces the elastic cushion 19 against its elastic restoring force and its own weight to the outside through the recess 9. The cushions 19 are pivoted or deformed to the outside, so to speak, like a rigid swing with elastic pivot joint. In this way, via the selected movement of the handle 5 through the recess 9, the cushions 19 can be deformed in the direction outside of the sieve basket 1. They protrude in sections (wedge-shaped) relative to the sieve basket side wall 3. The cushions 19 then rest against the inner wall of the container tray and fix the sieve basket 1. As can be seen from FIG. 20, for example, the cushions 19 in the fixed position cannot move back in the width direction into the interior of the sieve basket 1. The connection web 18, which can only be moved in the height direction and rests against the back of the cushions 19, geometrically restricts the degree of freedom in the width direction.

If the handle 5 is now lifted from the fixed position against its own weight and the frictional force of the adjacent cushions 19 back into the carrying position, the contact pressure of the handle 5 on the cushions 19 is released and the cushions 19 move back to their non-deformed initial state. The sieve basket 1 is then no longer fixed in the container tray and can be removed from it.

The invention claimed is:

1. A sterilization sieve basket, which is provided and configured for insertion into and removal from a container tray, wherein at least one sieve basket handle is movably mounted on at least one sieve basket side wall, the sieve basket handle having a gripping portion which is connected, via a connection web oriented at an angle to the gripping portion, to a bearing portion on which the sieve basket handle is held on a bearing on a side of the sieve basket wall and is movable into at least one carrying position and into a fixed position, wherein the sterilization sieve basket further comprises at least one fixing portion and/or press-on portion or element spaced from the gripping portion and supported on the at least one sieve basket side wall and movable and/or deformable by selected movement of the sieve basket handle away from the sieve basket side wall in a direction toward an outside of the sterilization sieve basket such that the at least one fixing portion and/or press-on portion or element abuts against a container tray, wherein the sieve basket handle is configured as a two-sided lever and is pivotably hinged about a pivot joint with a rotational axis, and the sieve basket handle comprises the fixing portion and/or press-on portion or the element spaced from the rotational axis and the gripping portion spaced from the rotational axis for manual gripping of the sieve basket handle, wherein the fixing portion and/or press-on portion or element is arranged on one side of the rotational axis and the gripping portion is arranged on another side of the rotational axis, so that a pivoting movement of the gripping portion causes a pivoting movement of the fixing portion and/or press-on portion or element about the rotational axis in the same direction.

2. The sterilization sieve basket according to claim 1, wherein a recess is formed in the at least one sieve basket side wall in an area of the at least one sieve basket handle, through which the fixing portion and/or press-on portion or the element is movable and/or deformed by selected movement of the sieve basket handle in the direction toward the outside of the sterilization sieve basket.

3. The sterilization sieve basket according to claim 1, wherein the sieve basket handle is configured in the form of a straight lever, and/or a perpendicular distance between the gripping portion and the rotational axis is greater by a multiple greater than a perpendicular distance between the fixing portion and/or press-on portion or element and the rotational axis in order to form an effective lever arm.

4. The sterilization sieve basket according to claim 1, wherein the sieve basket handle comprises a plurality of fixing portions and/or press-on portions or elements, which have an equal perpendicular distance between the fixing portion and/or press-on portion or element on the one hand and the rotational axis on the other hand.

5. The sterilization sieve basket according to claim 1, wherein the fixing portion and/or press-on portion or the element comprises an attachment with inherent elasticity, and the attachment is coupleable to the fixing portion.

6. A sterilization sieve basket, which is provided and configured for insertion into and removal from a container tray, wherein at least one sieve basket handle is movably mounted on at least one sieve basket side wall, the sieve basket handle having a gripping portion which is connected, via a connection web oriented at an angle to the gripping portion, to a bearing portion on which the sieve basket handle is held on a bearing on a side of the sieve basket wall and is movable into at least one carrying position and into a fixed position, wherein the sterilization sieve basket further comprises at least one fixing portion and/or press-on portion or element spaced from the gripping portion and supported on the at least one sieve basket side wall and movable and/or deformable by selected movement of the sieve basket handle away from the sieve basket side wall in a direction toward an outside of the sterilization sieve basket such that the at least one fixing portion and/or press-on portion or element abuts against a container tray, wherein the sterilization sieve basket comprises at least one extension module of the sieve basket handle, which has the bearing, the sieve basket handle mounted in the bearing and an extension structure, and wherein the extension module is fastened to the sieve basket wall as a separate module by the extension structure in a form-fitting and/or material-fitting manner.

7. The sterilization sieve basket according to claim 6, wherein the sterilization sieve basket has at two opposite rim/edge portions, a respective sieve basket handle and an associated fixing portion and/or press-on portion or element to be movable and/or deformable in the selected movement in opposite directions, respectively, outside of the sterilization sieve basket.

8. A sterilization sieve basket system comprising:
the sterilization sieve basket according to claim 1; and
a sterilization sieve basket lid.

9. A container system comprising a container and a sterilization sieve basket according to claim 1, wherein the sterilization sieve basket is insertable into a container tray of the container and is adapted in such a way that the fixing portion and/or press-on portion or the element in the fixed position abuts an inner wall of the container tray and braces the sterilization sieve basket against the container tray and thus positionally fixes and secures the sterilization sieve basket in the container.

10. The sterilization sieve basket according to claim 1, wherein the sieve basket handle is pivotably mounted on the at least one sieve basket side wall.

11. The sterilization sieve basket according to claim 2, wherein the fixing portion and/or press-on portion or the element that is movable and/or deformable by the selected movement of the sieve basket handle projects outward in the fixed position relative to the sieve basket side wall.

12. The sterilization sieve basket according to claim 7, wherein the associated fixing portion and/or press-on portion or element protrude outward in the fixed position relative to an outer side of the sieve basket wall in two opposite directions.

13. The sterilization sieve basket according to claim 5, wherein the attachment comprises rubber, silicone and/or plastic as material or consists of rubber, silicone or plastic as material.

14. The sterilization sieve basket according to claim 5, wherein the attachment is attachable and/or chippable onto the fixing portion.

* * * * *